United States Patent
Wehmeyer et al.

(10) Patent No.: US 9,259,522 B2
(45) Date of Patent: Feb. 16, 2016

(54) DIALYSIS SUPPLY SYSTEMS AND RELATED COMPONENTS

(75) Inventors: Wolfgang Wehmeyer, Tubingen (DE); Dietmar Köhler, Aubstadt (DE); Matthias Brandl, Bad Königshofen (DE); Benedict Glaser, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 709 days.

(21) Appl. No.: 13/347,011

(22) Filed: Jan. 10, 2012

(65) Prior Publication Data
US 2012/0175296 A1 Jul. 12, 2012

Related U.S. Application Data

(60) Provisional application No. 61/431,224, filed on Jan. 10, 2011.

(30) Foreign Application Priority Data

Jan. 10, 2011 (DE) .......................... 10 2011 008 223

(51) Int. Cl.
*B01D 61/30* (2006.01)
*A61M 1/16* (2006.01)
*B01D 61/28* (2006.01)
*B01D 61/32* (2006.01)
*A61M 1/14* (2006.01)
*A61M 1/36* (2006.01)

(52) U.S. Cl.
CPC .............. *A61M 1/1654* (2013.01); *A61M 1/14* (2013.01); *A61M 1/168* (2013.01); *A61M 1/1672* (2014.02); *A61M 1/1656* (2013.01); *A61M 1/3621* (2013.01); *A61M 2205/12* (2013.01); *A61M 2205/126* (2013.01); *A61M 2205/128* (2013.01)

(58) Field of Classification Search
CPC . A61M 1/3621; A61M 2205/12; A61M 1/14; A61M 1/1656; A61M 2205/126; A61M 2205/128; A61M 1/1654; A61M 1/1672; A61M 1/168
USPC ......... 210/645, 646, 650, 106, 109, 134, 143, 210/252, 257.1, 257.2, 258, 321.6, 321.69, 210/321.71, 420, 541
See application file for complete search history.

(56) References Cited

U.S. PATENT DOCUMENTS 4,181,694 A * 1/1980 Hashino et al. .................. 264/41
5,015,389 A * 5/1991 Portillo, Jr. .................... 210/646

(Continued)

FOREIGN PATENT DOCUMENTS

DE 4203905 12/1993
DE 19933223 A1 1/2001

(Continued)

OTHER PUBLICATIONS

Acumen, "Acute Dialysis Machine Brief Operating Instructions," Software Version 1.0, pp. 1-146, Jan. 1996.

(Continued)

*Primary Examiner* — John Kim
(74) *Attorney, Agent, or Firm* — Fish & Richardson P.C.

(57) ABSTRACT

A dialysis supply system that includes a central dialysis liquid manufacturing unit, a dialysis treatment unit, a valve arrangement, and a hydraulic module.

21 Claims, 4 Drawing Sheets

(56) References Cited

U.S. PATENT DOCUMENTS

| | | | |
|---|---|---|---|
| 5,616,248 A * | 4/1997 | Schal | 210/647 |
| 5,972,223 A * | 10/1999 | Jonsson et al. | 210/647 |
| 6,251,279 B1 * | 6/2001 | Peterson et al. | 210/636 |
| 6,645,166 B2 | 11/2003 | Scheunert et al. | |
| 8,858,488 B2 * | 10/2014 | Kelly et al. | 604/6.11 |
| 8,920,362 B2 * | 12/2014 | Childers et al. | 604/29 |
| 2005/0085760 A1 | 4/2005 | Ware et al. | |
| 2005/0230292 A1 | 10/2005 | Beden et al. | |
| 2008/0296226 A1 | 12/2008 | Gotch | |
| 2009/0012456 A1 * | 1/2009 | Childers et al. | 604/29 |
| 2009/0071911 A1 | 3/2009 | Folden et al. | |
| 2009/0101550 A1 | 4/2009 | Muller et al. | |
| 2009/0101566 A1 | 4/2009 | Crnkovich et al. | |
| 2010/0130906 A1 * | 5/2010 | Balschat et al. | 604/6.09 |
| 2010/0133153 A1 | 6/2010 | Beden et al. | |
| 2010/0181235 A1 | 7/2010 | Fava et al. | |
| 2010/0192686 A1 | 8/2010 | Kamen et al. | |
| 2011/0009797 A1 * | 1/2011 | Kelly et al. | 604/6.1 |
| 2012/0022440 A1 * | 1/2012 | Childers et al. | 604/29 |

FOREIGN PATENT DOCUMENTS

| | | |
|---|---|---|
| DE | 102006050272 A1 | 5/2008 |
| DE | 102009058681 A1 | 6/2011 |
| EP | 0436855 | 6/1994 |
| WO | WO 2004/009158 | 1/2004 |
| WO | WO 2006/074429 | 7/2006 |

OTHER PUBLICATIONS

International Search Report and Written Opinion; Application No. PCT/EP2012/000085; mailed Apr. 18, 2012; Applicant Fresenius Medical Care Deutschland GmbH; pp. 1-7.

Manns, Markus et al, "The acu-men: A new device for continuous renal replacement therapy in acute renal failure," Kidney International, vol. 54, pp. 268-274, 1998.

Operator's Manual—2008T Hemodialysis Machine; pp. 1-222 (2008).

Operator's Manual—Fresenius 2008K Hemodialysis Machine (2000).

* cited by examiner

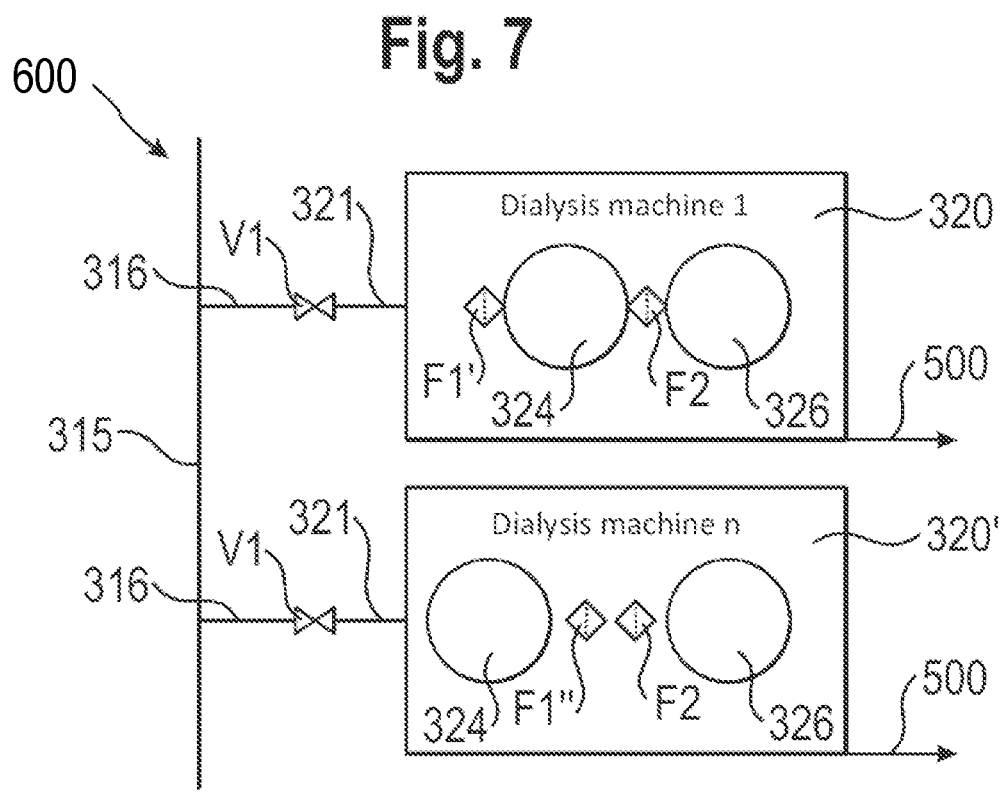
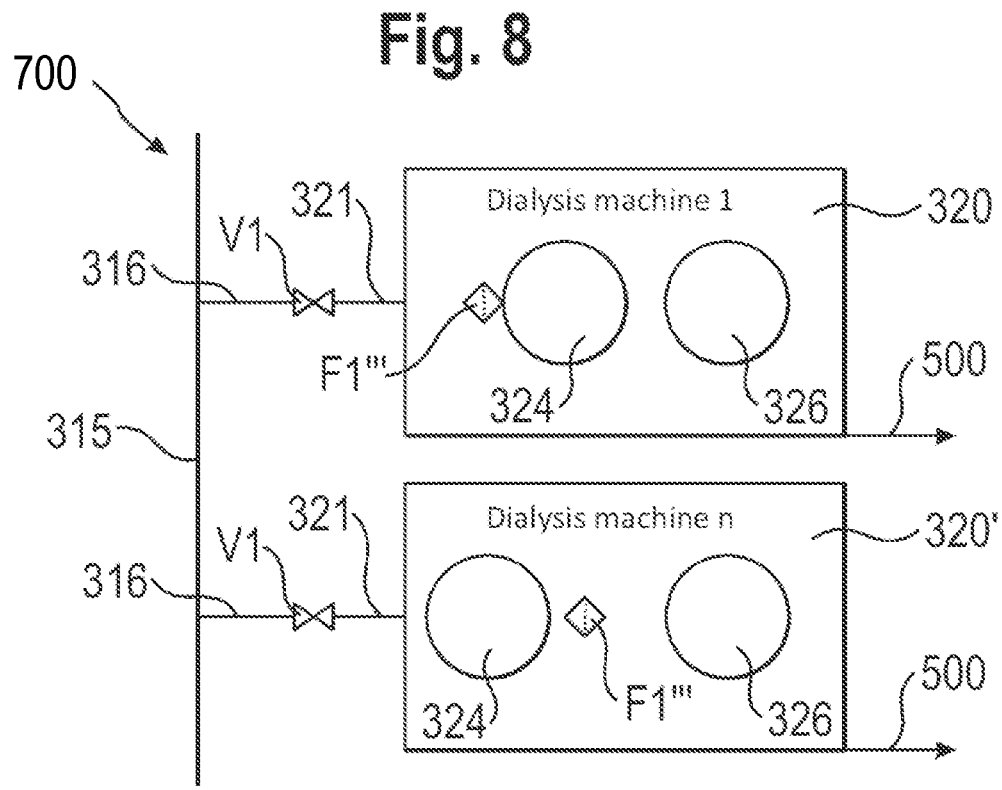

DIALYSIS SUPPLY SYSTEMS AND RELATED COMPONENTS

CROSS-REFERENCE TO RELATED APPLICATIONS

This application claims the benefit of U.S. Application Ser. No. 61/431,224, filed on Jan. 10, 2011, and claims priority under 35 U.S.C. §119(a) to German Application No. 10 2011 008 223.9, filed on Jan. 10, 2011. Each of the above-noted applications is incorporated by reference herein.

TECHNICAL FIELD

This disclosure relates to dialysis supply systems and related components.

BACKGROUND

Central supply systems for providing dialysis liquid (also referred to as dialysate) or dialysis liquid concentrates (also referred to as dialysate concentrates) are installed in some dialysis centers. The centrally manufactured liquids or liquid concentrates are typically delivered via a supply line system to individual treatment stations. Dialysis liquid is used at the treatment stations to purify blood circulating in an extracorporeal blood circuit connected to a dialysis machine. In systems that utilize a dialysis liquid concentrate, the dialysis liquid concentrate is delivered via the supply line and is used to manufacture a dialysis liquid to be used for treatment. The liquid concentrate is supplemented with additional solution components and diluted at the treatment station, which provides the prepared dialysis liquid for blood treatment. The used or spent dialysis liquid is often times directed away from the treatment station via a return fluid line system of the supply circuit and can be disposed of centrally. Alternatively, the spent dialysis liquid can be delivered directly into a drainage system.

A central supply system of the type described above renders many components found in conventional dialysis machines of treatment stations (referred to as "bedside monitors") unnecessary for manufacturing dialysis liquid. The central supply system can, for example, deliver pre-heated dialysis liquid to the treatment station such that no dialysis liquid temperature setting units are required at the treatment station or such that the treatment stations can be operated at a relatively low power. Degassing units within the dialysis machine can similarly be omitted, as the functionality of these units can be performed by the central supply system.

The installation of bedside monitor systems in dialysis treatment centers results in a need to regularly disinfect the supply system and the individual treatment stations. In some instances, contaminants can enter the line system and spread to a bedside station or to a treatment station. For safety reasons, disinfection programs can be observed to ensure that the total supply system is not contaminated. Disinfection can, in some cases, require a significant amount of time and a large effort depending on the size and construction of the line system.

In certain cases, a sterile filter is disposed between the dialysis station to the supply system in order to reduce the risk of contamination to a central dialysis tank.

In some cases, a buffer tank is provided to prevent a backflow of contaminated liquid into the supply line system. In some instances, ultrafilters can be included within the fluid circuit on the dialysate side of the treatment station to further prevent backflow.

The disinfection process for a dialysis treatment station that is supplied with fresh water by a ring line system can include decoupling the dialysis machine from the fresh water system via a valve control, and then disinfecting the dialysis machine with heat or chemical additives while operating the dialysis machine in a circulation mode.

SUMMARY

Certain dialysis supply systems described herein can advantageously be operated simply, safely, and hygienically. Furthermore, disinfection of the dialysis supply systems can be simplified, and contamination of fluid line systems coupled to bedside treatment stations can be prevented.

In one aspect of the invention, a dialysis system includes at least one dialysis treatment unit and a central dialysis liquid manufacturing unit that can be indirectly or directly coupled via at least a first conduit to the at least one dialysis treatment unit. The first conduit is configured to transport dialysis liquid from the central dialysis liquid manufacturing unit toward the dialysis treatment unit. At least one valve that is controllable by a control unit and is operable to control a flow of liquid through the dialysis system, including an inflow of dialysis liquid to the dialysis treatment unit, an outflow of dialysis liquid from the dialysis treatment unit, a rinsing flow, a cleaning flow, and a disinfection flow. A single-use hydraulic module is configured to be connected to the dialysis treatment unit and is operable with the dialysis treatment unit to conduct, convey, process, mix, and/or equalize dialysis liquid.

In another aspect of the invention, a dialysis supply system includes at least one central manufacturing unit that is operable to provide dialysis liquid and includes at least one conduit through which the dialysis liquid flows. The dialysis supply system includes at least one dialysis treatment unit, which includes at least one second conduit via which the dialysis treatment unit can be indirectly or directly coupled to the first conduit. The dialysis supply system includes a valve system including at least one valve operable to control one or more flows including an inflow and an outflow of dialysis liquid to the dialysis treatment unit, a rinsing flow, a cleaning flow, and a disinfection flow. Each flow is operable to run for different modes of a dialysis treatment, and the disinfection flow is operable to run for different disinfection modes. The valve system is controllable by a control unit. At least one hydraulic module is operable to perform one or more operations including conducting, conveying, processing, mixing, and equalizing dialysis liquid in the dialysis treatment unit. The hydraulic module is a single-use hydraulic module.

In some implementations, the hydraulic module is an ultrafiltration module.

In some implementations, the dialysis supply system is a central dialysis liquid supply system (e.g., as is the case for a dialysis liquid supply system located at a hospital, or in a dialysis station located at a hospital or in a dialysis center including a central manufacturing unit for providing dialysis liquid).

In certain implementations, one or more components of the dialysis supply system can be stationary components. Accordingly, the central manufacturing unit can be configured for preparing dialysate liquid centrally and in consideration of the setup of the dialysis center or the dialysis station. Alternatively, the dialysis treatment units may generally be configured as mobile units (e.g., as is the case for mobile and transportable treatment monitors).

The terms dialysis liquid and dialysate are not intended to be restricted only to ready-to-use dialysis solutions, but rather, the terms dialysis liquid and dialysate also include dialysis concentrates and dialysis solutions that need to be supplemented with additional additives (e.g., directly at the treatment location). A dialysate-conducting line can thus, for example, be a line that conducts a ready-to-use dialysis solution or a line that conducts components of a dialysis solution, such as dialysis solution concentrate.

In certain implementations, the first conduit forms a central ring line through which the dialysis liquid can be provided and conveyed. The dialysis treatment units can be coupled indirectly and/or directly to the first conduit. The coupling for this purpose can be provided with or be in communication with a corresponding sealing device. In some implementations, the coupling can be provided with a valve via which the inflow of dialysis liquid to the dialysis treatment unit can be blocked and/or released.

In some implementations, the valve is operable to control one or more flows including the inflow and outflow of dialysis liquid to the dialysis treatment unit, a rinsing flow, a cleaning flow, and a disinfection flow. Each flow cycle is operable to run for different operating modes of the dialysis treatment, and the disinfection flow is operable to run for different disinfection modes. In this manner, a control unit can be a decentralized control unit (e.g., a control unit included within the dialysis treatment unit). Alternatively, the control unit can be a central control unit included within the dialysis supply system.

In some implementations, cleaning of the dialysis machine is advantageously not required after a treatment procedure since all contaminated parts can be discarded. Furthermore, back contamination of the ring line and of the central supply station is minimized since propagation of contamination across several treatment units (as is the case for many existing dialysis machines) is prevented due to discarding of one or more disposable elements.

In some implementations, at least one hydraulic module is provided as exclusive single means performing one or more operations including conducting, conveying, processing, mixing and equalizing the dialysis liquid in the dialysis treatment unit.

In certain implementations, at least one blood module is provided to perform one or more operations including conducting, conveying, and processing blood in the dialysis treatment unit. In some instances, the blood module is a single-use, disposable module.

In some implementations, due to the use of disposable hydraulic modules, it is advantageously possible to use disposables on both the blood side and the dialysate side of the system. This allows a fast and simple changing of patients since single-use consumables can considerably simplify the disinfection process. Since materials that come into contact with potentially infectious materials on the treatment unit side are disposed of after the treatment, only the central dialysate feed line or the ring line may need to be disinfected. In some implementations, the main source of germs in the dialysate feed line is the liquid-filled line, itself, and not the patient. Therefore, disinfection may be performed considerably less often than the patient is changed, saving time and costs. In some instances, automatic processes can be implemented for disinfecting ring lines.

In some implementations, transfer of germs from the patient to the dialysate feed line or to the ring line system is minimized simply by the flow direction. The filters between the feed line and the blood line primarily protect the patient from the transfer of germs and endotoxins (i.e., toxins produced by germs from the dialysate feed line) into the blood. The consumed and thus potentially contaminated dialysate is disposed of via a second line.

In one aspect of the invention, at least one separation membrane or one filter is provided between the dialysate and the blood, thus preventing the transfer of germs and endotoxins to the patient. In some cases, a possible failure of the first filter or of the first separation membrane (as could be the case, for example, for a rupture of the first filter) can be countered by a second separation membrane or by a second filter. In some instances (e.g., for a case of a simple hemodialysis treatment in which the mass transfer between blood and dialysate only takes place via the dialyzer membrane, that is, via a filter), it can advantageously be sufficient to use an ultrafilter. For hemodiafiltration treatments, some of the exchange volume is added directly to the blood, with this added liquid quantity being removed again in exchange via the dialyzer, which can result in a need for a second filter that filters the dialysate before it is added directly to the blood.

In some implementations, a two-stage filtration of the dialysate may be implemented for a process of so-called online priming. In this process, the blood-conducting fluid portion of the disposable is cleaned using a rinsing liquid before the start of a dialysis treatment. Dialysate is suitable as the rinsing liquid. In common priming processes, the blood-conducting portion of the extracorporeal circuit can be connected to a dialysate source and a pump so that it can be rinsed. In online priming, the rinsing liquid (e.g., dialysate) is flowed by a corresponding pump and valve settings via the blood treatment filter into the blood-conducting portion of the extracorporeal circuit. The blood-conducting portion of the extracorporeal circuit is subsequently rinsed. The blood-conducting portion of the extracorporeal circuit is already protected from contamination by filtration at the blood treatment filter. However, two filtration stages may be implemented for safety reasons, for example, if liquid should cross over into the blood-conducting portion. An additional filtration stage may therefore be installed in the dialysate-conducting portion upstream of the blood treatment filter for online priming.

In some implementations, dialysis treatments can be performed simply and safely when fluid circuits of the dialysis treatment units are disposable. Furthermore, the number of dialysis treatments performed in a given time period can be increased (i.e., the intervals between treatments can be shortened) since a cleaning and/or disinfecting procedure can be avoided. Accordingly, a repeated use of a hydraulic module and components of a hose kit can be provided as sterile components.

In certain implementations, at least one filter is provided to prevent back contamination and for filtering of the dialysis liquid.

In some implementations, at least one filter is a filter that can be used multiple times and that is positioned upstream of the hydraulic module and upstream of the blood module in a direction of the dialysate flow.

In certain implementations, at least one filter is a disposable filter.

In some implementations, at least one filter is a component of the hydraulic module and/or of the blood module.

In certain implementations, at least one first filter and at least one second filter are provided.

In some implementations, the at least one first filter is a filter that can be used multiple times and that is positioned upstream of the hydraulic module and upstream of the blood module in the direction of the dialysate flow.

In certain implementations, the at least one first filter is a disposable filter.

In some implementations, the at least one second filter is a disposable filter.

In certain implementations, the at least one second filter is a component of the hydraulic module and/or of the blood module.

In some implementations, both the hydraulic module and the blood module each include a filter.

In certain implementations, the filter is an ultrafilter. The ultrafilter, in some implementations, is a hollow fiber filter and that includes a membrane having a mean pore size of approximately 0.1-0.5 μm (e.g., approximately 0.2 μm).

In certain implementations, the dialysis supply system includes at least three dialysate-conducting lines branching off from the at least one first conduit and through which dialysis liquid flows. The valve system includes at least three valves, wherein one respective valve is disposed in a dialysate-conducting line such that the dialysate can be supplied to the dialysate treatment unit.

In some implementations, the dialysate-conducting lines can be coupled to the dialysis treatment unit and are lines through which dialysis liquid can flow. Disinfection liquid can also flow through the dialysate-conducting lines when the system operates in a disinfection mode.

In certain implementations, a first two dialysate-conducting lines are coupled to a first region of the filter that is separated from a second region of the filter by a membrane, and a third dialysate-conducting line is coupled to the second region of the filter such that the two first lines are bypassable by the third dialysate-conducting line. The third dialysate-conducting line thus forms a bypass line with respect to the first two dialysate-conducting lines.

In some implementations, a valve arrangement is provided by the at least three valves. The valve arrangement can be controlled by a control unit such that the filter can be disinfected on one or both sides and/or through the membrane of the filter.

In certain implementations, the valve arrangement can be controlled by a control unit such that the filter can be disinfected from both sides of the membrane of the filter via disinfection liquid flowing through the valve arrangement.

In some implementations, in a first mode, a first valve is arranged in dialysate-conducting lines that are coupled to a first side of the filter and is changeable to an open state, whereas a second valve is arranged in dialysate-conducting lines that are coupled to a first side of the filter and is closable, and a third valve disposed in a third dialysate-conducting line and coupled to a second side of the filter is closable. In a second mode, the first valve is closable, the second valve is switchable to an open state, and the third valve is switchable to an open state.

In certain implementations, the dialysis treatment unit is separable by at least one fourth valve from the at least one first conduit that conducts disinfection liquid.

In some implementations, the at least one fourth valve is positioned upstream of the hydraulic module and downstream of the filter in a dialysate-conducting line coupled to the second side of the filter, and the filter is arranged between at least two valves of the valve system. In some cases, two valves are positioned on the first side of the filter and two valves are positioned on the second side of the filter.

In certain implementations, the first side of the filter is the side that is remote from the hydraulic module (i.e., the dialysate still has to cross over the membrane of the filter to reach the hydraulic module). The second side of the filter is accordingly the side facing the hydraulic module. Accordingly, a line is advantageously available with the third line, which can be used as the conducting means in a disinfecting mode. The first mode can thus, for example, be the normal treatment mode, with the first line serving the supply of the dialysate and the second and third lines being blocked by the valves therein. In the second mode, which is a cleaning mode and/or disinfecting mode, the first line is blocked via the valve located therein, such that the connection line to the dialysis treatment unit is advantageously blocked via a fourth valve located therein. The second and third lines are open in this mode such that a flow to the filter is possible at both sides of the membrane. Thus, the filter can be used multiple times for cleaning and/or disinfecting and without problems. The control of the valves can take place, for example, via a control unit of the conducting means. This control unit can be the central control unit of the conducting means.

In another aspect of the invention, a hydraulic module having the above-stated features can be included within the dialysis supply system.

In another aspect of the invention, a disposal hose kit includes at least one hydraulic module having the above-stated features and a blood module integrated with the disposable hose kit.

In certain implementations, the hose kit is advantageously provided for use in a dialysis treatment unit. In such instances, the dialysis treatment unit is provided with corresponding mounts to which the hose kit can be connected via mating parts.

In another aspect of the invention, a disposal cassette includes at least one hydraulic module that has the above-stated features and a blood module that is integrated with the disposable cassette.

In a further aspect of the invention, a disposable cassette includes a hydraulic module and a blood module that are integrated with the disposable cassette. The disposable cassette further includes at least one filter that is configured to substantially prevent contamination between a central dialysis liquid manufacturing unit and the blood module when the disposable cassette is fluidly connected to the central dialysis liquid manufacturing unit.

In some implementations, the disposable cassette is provided for use in a dialysis treatment unit. In such instances, the dialysis treatment unit is provided with corresponding mounts to which the cassette can be coupled via corresponding mating parts.

In certain implementations, the hydraulic module (in particular, the hydraulic module of the hose kit and/or the hydraulic module of the cassette) includes functional elements for processing the dialysis liquid. The hydraulic module can, for example, include an equalizing unit for equalizing fresh and consumed dialysate, a heater for heating the fresh dialysate, a pressure sensor, a temperature sensor, a blood leak detector, a sensor unit for determining the clearance, and/or a pump for pumping the dialysate and the ultrafiltrate. The sensor unit does not need to be included within the hydraulic module; rather, the sensor unit can be included within the dialysis treatment unit. When the hydraulic module is configured as a disposable module, the hydraulic module includes interfaces that couple the hydraulic module to the sensor unit.

In some implementations, the blood module (in particular, the blood module of the hose kit and/or the blood module of the cassette) includes functional elements for processing patient blood that is to be treated. The blood module can, for example, include a blood temperature monitor, a temperature sensor, a sensor system for analyzing the composition of the blood (e.g., hemoglobin content, plasma portion, blood volume, and anticoagulant content), a gas bubble detector, a liquid detector, and an ultrasound sensor system. The sensor units used do not need to be included within the blood module; rather, the sensor unit can be included within the dialysis treatment unit. When the blood module is configured as a disposable module, the blood module includes interfaces that couple the blood module to the sensor unit.

In certain implementations, the dialysis treatment filter can be integrated into the blood module.

In another aspect of the invention, the dialysis treatment unit is a dialysis machine or a dialysis treatment monitor and includes a hydraulic module, a disposable hose kit, and/or a disposable cassette.

Other aspects, features, and advantages of the invention will be apparent from the description, the drawings, and the claims.

DESCRIPTION OF DRAWINGS

FIG. 7 is a schematic representation of an additional dialysis supply system.

FIG. 8 is a schematic representation of another dialysis supply system.

DETAILED DESCRIPTION

Figure 1:
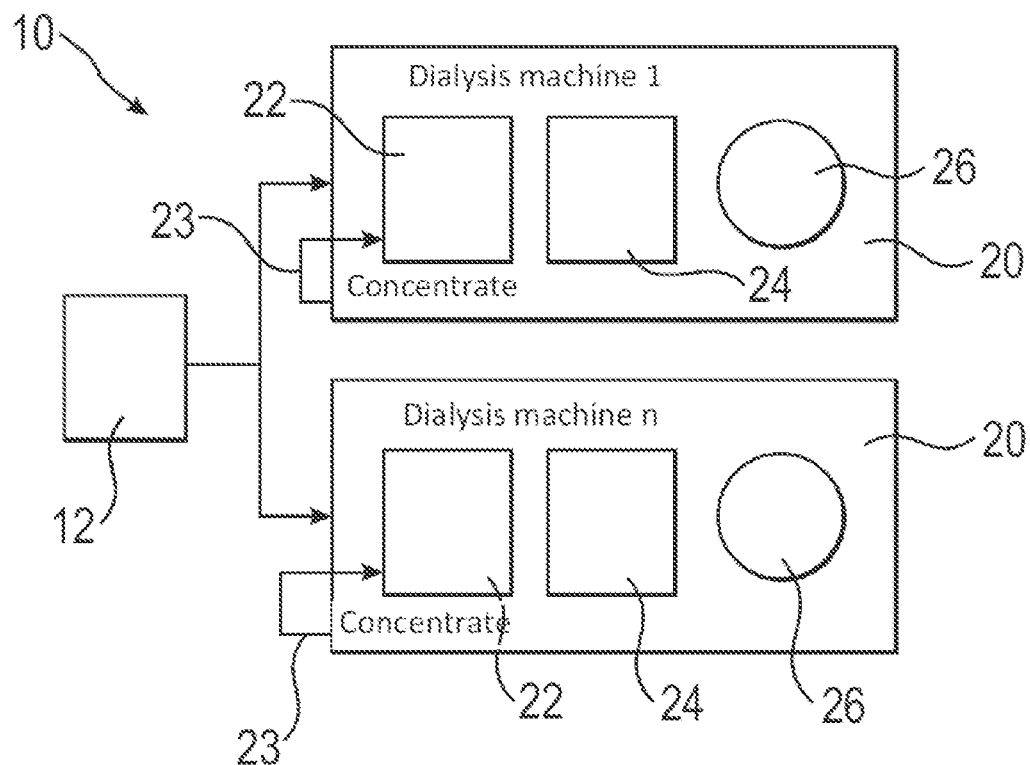
FIG. 1 is a schematic representation of a dialysis supply system.

As shown in FIG. 1, a dialysis supply system 10 includes a central supply unit 12 and one or more (n) dialysis machines 20. A supply of fresh water is typically provided to the central supply unit 12 by a central stationary reverse osmosis plant or ultrapure water plant. In contrast, preparation of the dialysate, monitoring of the ultrafiltration, and establishing of the extracorporeal blood circuit occurs in a decentralized manner and via a separate treatment unit (e.g., via one of the dialysis machines 20).

Accordingly, the dialysis machine 20 includes a dialysate module 22 that is operable to prepare dialysate, a hydraulic module 24 that is operable to monitor the ultrafiltration, and a blood module 26 that is operable to establish the extracorporeal blood circuit. The dialysate module 22 can prepare the dialysate by mixing a dialysate concentrate 23 with fresh water supplied from the central supply unit 12.

The fluid conduits on the dialysate side of the dialysis supply system 10, including the fluid conduits coupled to the dialysate module 22 and to the hydraulic module 24, can be used multiple times. Thus, those fluid conduits can be cleaned, disinfected, and decalcified at regular intervals. In contrast, the fluid conduits included within the extracorporeal blood circuit (i.e., those coupled to or included within the blood module 26) are provided for single use and are therefore disposable.

Figure 2:
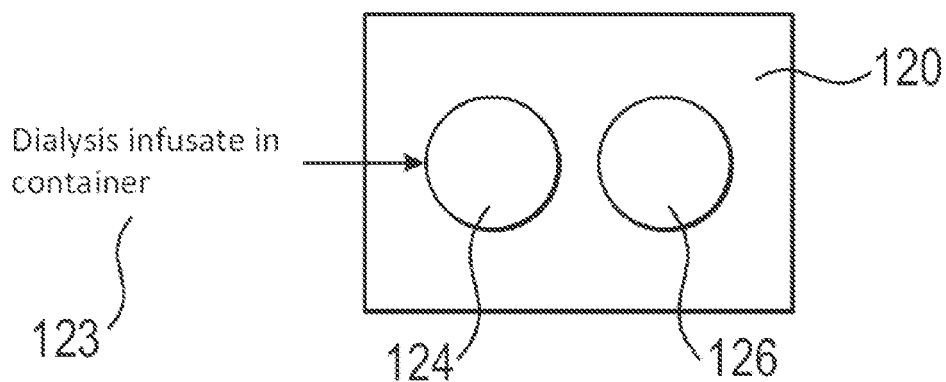
FIG. 2 is a schematic representation of a CRRT system.

As shown in FIG. 2, a continuous renal replacement therapy (CRRT) unit 120 includes container 123 that holds dialysate and infusate instead of the central supply unit 12 of FIG. 1. In some implementations, the CRRT unit 120 is used in a treatment environment in which the location and usage frequency can vary considerably. One application of the CRRT unit 120, for example, is for the treatment of acute renal failure of intensive-care patients. Given the importance of cleanliness and sterility in a typical intensive-care unit, the CRRT unit 120 is configured so that its components can be disinfected. Accordingly, disposable hydraulic modules 124 and disposable blood modules 126 are typically used with the CRRT unit 120. A fast and reliable installation and start-up of the CRRT unit 120 can thus occur even after a relatively long idle time since the fluid conduits included within the CRRT unit 120 are disposable and thus do not need to be cleaned, disinfected, or decalcified.

Figure 3:
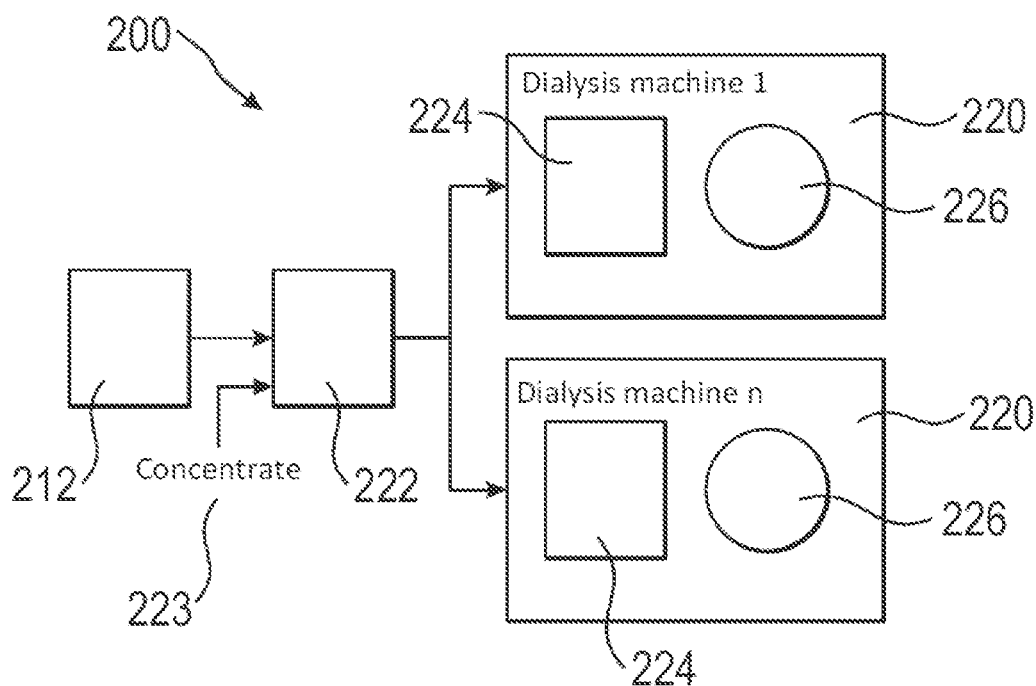
FIG. 3 is a schematic representation of a bedside monitor system.

As shown in FIG. 3, a bedside dialysis system 200 includes a central supply unit 212 and a central dialysate preparation unit 222 in which dialysate concentrate 223 and fresh water are mixed to form dialysate. One or more (n) dialysis machines 220 each have a hydraulic module 224 and a blood module 226 that are of generally the same construction and that can be configured in the same manner as the hydraulic module 24 and the blood module 26 of FIG. 1. The fluid conduits on the dialysate side of the bedside dialysis system 200 are provided for multiple use. Accordingly, the components of the hydraulic module 224 can be cleaned, disinfected, and decalcified at regular intervals. The components of the blood module 226 are disposable, single-use components.

Figure 4:
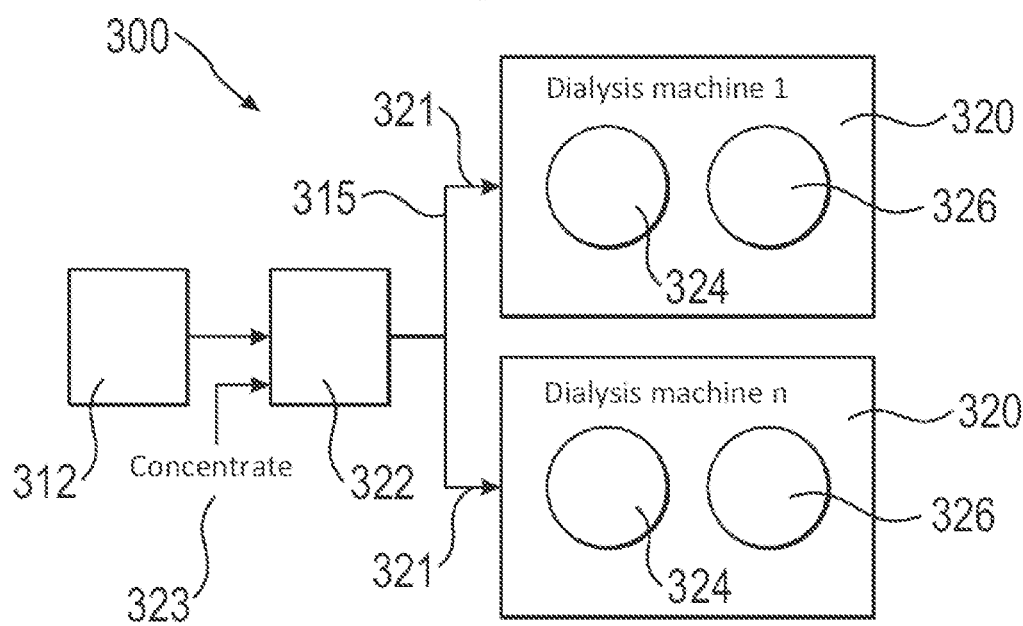
FIG. 4 is a schematic representation of a dialysis supply system.

As shown in FIG. 4, a central dialysis supply system 300 includes a central supply unit 312 and a central dialysate preparation unit 322 in which dialysate concentrate 323 and fresh water are mixed to form dialysate. In the implementations of FIGS. 4-8, the disposable modules of the system 300 are shown as circles.

In some implementations, dialysate can be defined as a fluid that has at least 50% of a desired amount of sodium and bicarbonate for a dialysate treatment.

Still referring to FIG. 4, the dialysis machines 320 are supplied with dialysate via connection lines 315, as indicated by arrows 321. The connection lines 315 can, for example, form a stationary ring line.

The fluid conductors (i.e., the hydraulic module 324 and the blood module 326) that are in at least indirect contact with a patient and/or the patient's blood are provided as single-use (i.e., disposable) components.

In some implementations, the hydraulic module 324 includes components for processing the dialysis fluid. For example, the hydraulic module 324 may include an equalizing unit for equalizing fresh and consumed dialysate, a heater for heating the fresh dialysate, a sensor for determining a clearance, and a pump for circulating the dialysate and the ultrafiltrate. The hydraulic module may further include one or more components including a pressure sensor, a temperature sensor, and a blood leak detector.

In some implementations, the blood module 326 includes components for processing or analyzing the patient's blood. For example, the blood module 326 may include a blood temperature monitor, a temperature sensor, a sensor system for analyzing the composition of the blood (e.g., hemoglobin content, plasma portion, blood volume, and anticoagulant content), a gas bubble detector, a fluid detector, and an ultrasound sensor system.

In some implementations, the hydraulic module 324 and the blood module 326 are disposable and therefore include disposable connections for the sensor system and the actuator system.

In some implementations, the modules 324 and 326 are housed separate from one another and process different fluids. Alternatively, the modules 324 and 326 can be integral within one unit. Accordingly, the modules 324 and 326 can thus be combined to form a disposable cassette. In some implementations, the modules 324 and 326 are provided as integral to a disposable hose kit.

A dialyzer (not shown) and an infusion port of the substitute for hemofiltration or hemodiafiltration therapies may be transmodular interfaces that can be coupled to both modules 324 and 326.

Figure 5:
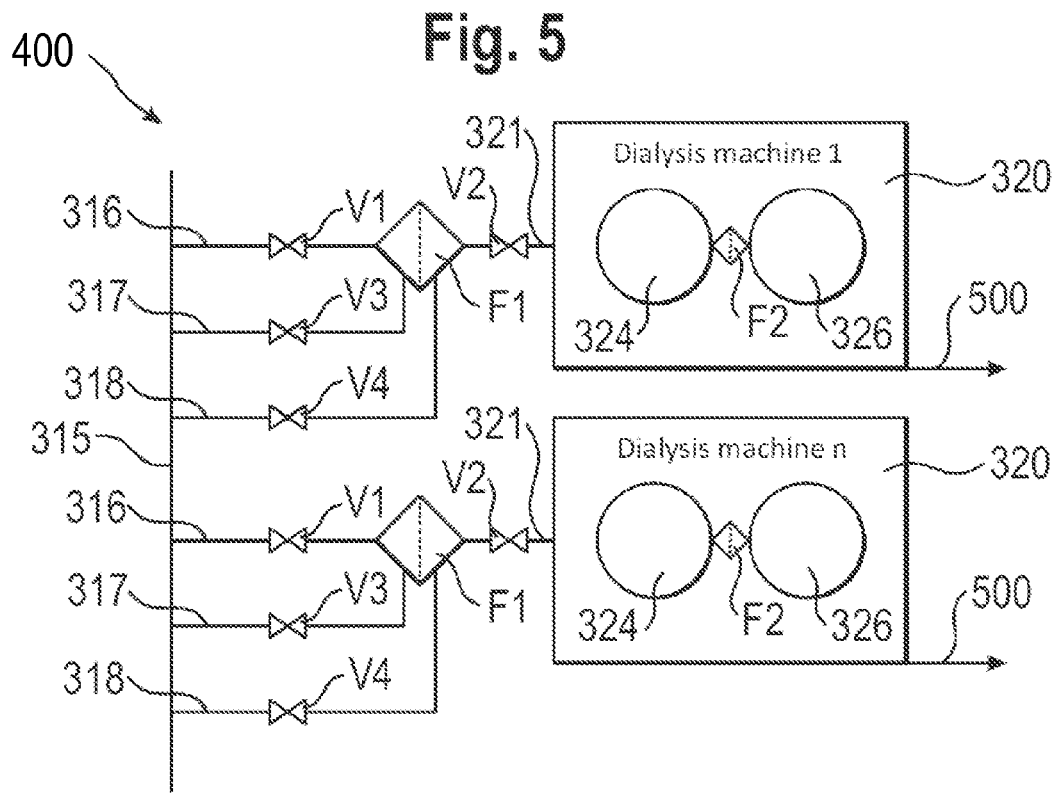
FIG. 5 is a schematic representation of a dialysis supply system.

FIG. 5 displays another dialysis supply system 400 including the dialysis machines 320 of FIG. 4. A valve system including valves V1, V3, and V4 can be used to adjust the inflow of the dialysate and is provided in the ring line system 315. A filter F1 is reusable and is provided as an integral component of the ring line 315. In some implementations, the filter F1 only needs to be replaced or cleaned after a specific idle time. The filter F1 separates lines 316 and 317 including the valves V1 and V3 from line 321 including valve V2. A bypass to the lines 316 and 317 is provided as line 318, which can be blocked via the valve V4.

The lines 316, 317, 318, the valves V1, V2, V3, V4, and the filter F1 are constructed and arranged in an analogous manner for each of the dialysis machines 320.

An additional filter F2 is further provided between the hydraulic module 324 and the blood module 326 and is disposable.

In some implementations, the configuration of the dialysis supply system 400 allows the ring line system 315 to be easily disinfected. The ring line system 315 is typically disinfected once per day (usually at night).

A first safety mechanism is provided by the disposable filter F2. An additional safety mechanism is further provided by the filter F1, whose function is checked after each disinfection process.

The valves V1 and V2 can be opened using a control unit to supply dialysate to the dialysis machine 320, which is coupled to the ring line system 315 via the line 321. Some or all of this fluid can flow through the filter F2 and can be used for a priming mode, a rinse back mode, a hemodiafiltration (HDF), or a hemofiltration (HF). A portion of the fluid that remains or a total fluid flow that has flown through the filter F2 can be used as the dialysate.

The valves V3 and V4 can be used for disinfecting the ring line system 315 when the dialysis supply system 400 is operating in the disinfection mode. They are preferably controlled via a central control unit of the ring line 315. The valve V2 is typically closed during disinfection of the ring line system 315.

Figure 6:
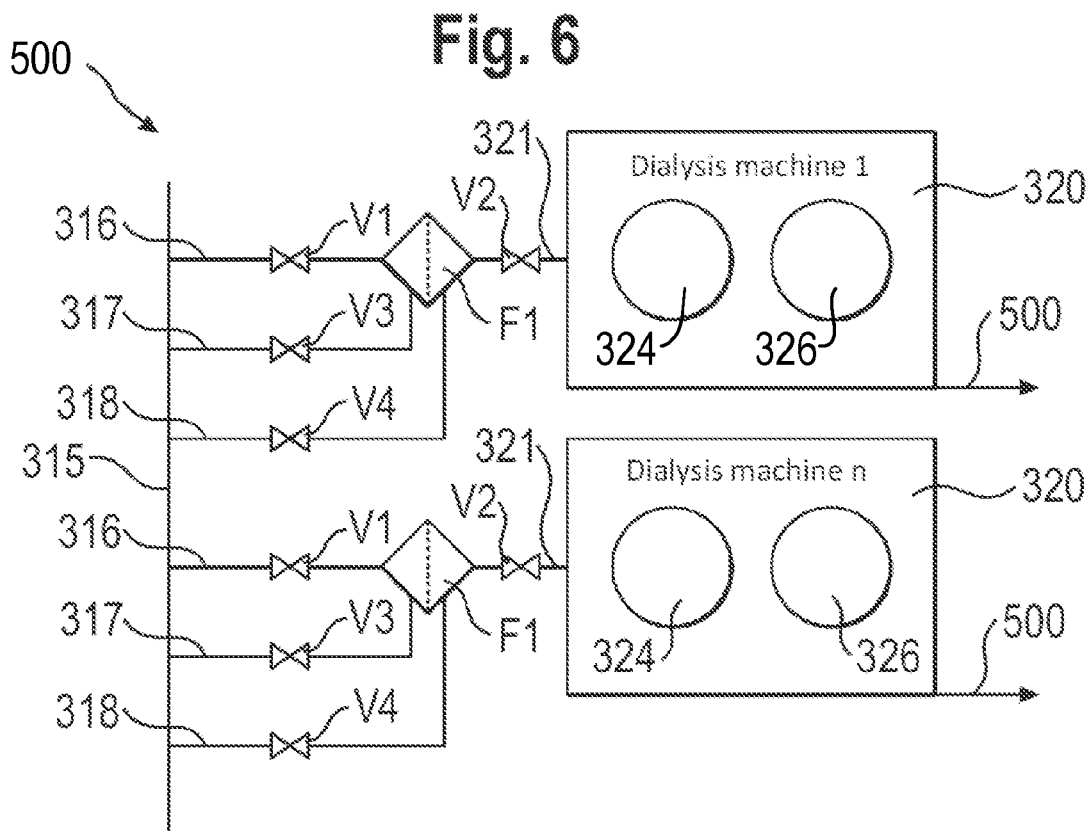
FIG. 6 is a schematic representation of another dialysis supply system.

FIG. 6 shows a dialysis supply system 500 that is slightly modified relative to the dialysis supply system 400 shown in FIG. 5 (like components are indicated by like reference numerals). The dialysis supply system 500 of FIG. 6 allows only a hemodialysis treatment.

The disposable filter F2 of FIG. 5 is omitted from the dialysis supply system 500 shown in FIG. 6. A priming can occur such that the filter F1 is used as a first ultrafilter, and the dialyzer is used as an additional ultrafilter. The dialysate is pumped from the dialysate side across the semipermeable membrane of the dialyzer to the blood side so that a priming can occur.

FIG. 7 shows another dialysis supply system 600 that is similar to the dialysis supply systems 400 and 500 of FIGS. 5 and 6 (like components are indicated by like reference numerals).

In the dialysis supply system 600 of FIG. 7, the reusable filter F1 of the dialysis systems 400 and 500 shown in FIGS. 5 and 6 is replaced by a disposable, single-use filter F1'. At least two single-use filters F1' and F2 are provided and are each configured as ultrafilters. The position of these single-use filters F1' and F2 can be upstream and/or downstream of the hydraulic module 324.

The upper dialysis machine 320 shows a first arrangement in which the single-use filter F1' is arranged upstream of the hydraulic module 324, and the second single-use filter F2 is arranged downstream of the hydraulic module 324.

A lower dialysis machine 320' shows a second arrangement in which both filters F1" and F2 are arranged downstream of the hydraulic module 324. The single-use filter F1" is therefore arranged downstream of the hydraulic module 324, and the second single-use filter F2 is arranged upstream of the blood module 326.

FIG. 8 shows a dialysis supply system 700 that is modified relative to the dialysis supply system 600 of FIG. 7 (like components are indicated by like reference numerals).

Similar to the implementation shown in FIG. 6, one of the two ultrafilters is omitted such that the dialysis supply system 700 of FIG. 8 can only operate in a hemodialysis treatment mode.

A priming can occur in that a filter F1''' is used as a first ultrafilter, and the dialyzer is used as an additional ultrafilter. The dialysate is pumped from the dialysate side across the semipermeable membrane of the dialyzer to the blood side such that the priming can occur.

The upper dialysis machine 320 shows a first arrangement in which the single-use filter F1'''0 is arranged upstream of the hydraulic module 324.

The lower dialysis machine 320' shows a second arrangement in which the single-use filter F1''' is arranged downstream of the hydraulic module 324.

FIGS. 5-8 thus show different arrangements of the filters F1, F1', F1", F1''', and F2, which are arranged with respect to the flow direction of the fresh dialysis fluid between and/or in front of individual modules 324 and 326. The filters F1, F1', F1", F1''', and F2 are ultrafiltration filters that are able to decontaminate delivered dialysate. Filters of various types (e.g., hollow fiber modules) can be used to perform such processes. In some implementations, a mean pore size of the filters can range from 0.1-0.5 μm. In some instances, the mean pore size is approximately 0.2 μm.

For hemodiafiltration treatments, present substitute, which has the same composition as dialysate used in hemodialysis, is infused into the blood conduits of the extracorporeal circuit. In some implementations, drop chambers are used within the blood circuit for this infusion. The addition of substitute into the blood conduit system can occur upstream and/or downstream of the filter. In some implementations, the substitute can be generated directly from the dialysate by performing an additional filtration step, as can be performed for online hemodiafiltration (online HDF) (e.g., by using the dialysis supply systems shown in FIGS. 5 and 7).

In some implementations, the dialysis treatment filters or dialyzers can be provided integrally with the blood module 326.

The dialysis machines 320 and 320' shown in FIGS. 5-8 include drainage lines 500 for the drainage of spent dialysate and that lead either to a central drain (not shown) or to a collection container, such as a bag for the spent dialysis solution.

Other implementations are within the scope of the following claims.

What is claimed is:

1. A dialysis supply system comprising:
   a plurality of dialysis treatment units;
   a central dialysis liquid manufacturing unit that can be coupled via at least a first conduit to the plurality of dialysis treatment units;
   at least one filter comprising a first region coupled to the central dialysis liquid manufacturing unit and a second region coupled to at least one of the dialysis treatment units, the first region of the filter being separated from the second region of the filter by a membrane;

a plurality of disposable, single-use hydraulic modules configured to be connected to the plurality of dialysis treatment units and operable with the plurality of dialysis treatment units to exclusively conduct dialysis liquid through the dialysis treatment units;

a plurality of disposable, single-use blood modules configured to be connected to the plurality of dialysis treatment units and operable with the plurality of dialysis treatment units to conduct blood through the dialysis treatment units;

a first valve arranged in a first fluid-conducting line coupled to the first region of the filter and to the first conduit;

a second valve arranged in a second fluid-conducting line coupled to the first region of the filter and to the first conduit; and a third valve arranged in a third fluid-conducting line coupled to the second region of the filter and to a hydraulic module of the plurality of hydraulic modules, wherein, in a first mode, a control unit operates the first, second, and third valves to transport liquid from the central dialysis liquid manufacturing unit through the first and second regions of the filter to the hydraulic module, and, in a second mode, the control unit operates the valves to transport liquid to at least one of the first and second regions of the filter without transporting liquid from the central dialysis liquid manufacturing unit to the hydraulic module, and wherein, in the second mode, the control unit operates the first, second, and third valves such that the first valve is closed, the second valve is open, and the third valve is closed.

2. The dialysis supply system of claim 1, wherein-at least one of-the first, second, and third valves is operable to control an inflow of dialysis liquid to the at least one of the plurality of dialysis treatment units, an outflow of dialysis liquid from the at least one of the dialysis treatment units, a rinsing flow, a cleaning flow, and/or a disinfection flow.

3. The dialysis supply system of claim 1, wherein the at least one filter is operable to substantially prevent backward contamination and/or to filter dialysis liquid.

4. The dialysis supply system of claim 3, wherein the at least one filter is a filter that can be reused and that is arranged upstream of the hydraulic module in a direction of dialysate flow.

5. The dialysis supply system of claim 3, wherein the at least one-filter is a single-use filter.

6. The dialysis supply system of claim 3, wherein the at least one filter is a component of the hydraulic module and/or one of the blood modules.

7. The dialysis supply system of claim 3, wherein the at least one filter is a hollow fiber filter, and the membrane comprises a mean pore size of approximately 0.1-0.5µm.

8. The dialysis supply system of claim 1, wherein the at least one filter is at least one first filter, and wherein the dialysis supply system comprises at least one second filter.

9. The dialysis supply system of claim 8, wherein the at least one first filter is reusable and is arranged upstream of the hydraulic module in a direction of dialysate flow.

10. The dialysis supply system of claim 8, wherein the at least one first filter is a single-use filter.

11. The dialysis supply system of claim 10, wherein the at least one second filter is a single-use filter.

12. The dialysis supply system of claim 8, wherein the at least one second filter is a component of the hydraulic module and/or one of the blood modules.

13. The dialysis supply system of claim 12, wherein the hydraulic module includes the first filter and the one of the blood modules includes the second filter.

14. The dialysis supply system of claim 1, wherein the first, second, and third valves are controllable by the control unit to control a flow of disinfection fluid through the first, second, and third valves in a manner that allows the disinfection fluid to flow through the first region of the filter, through the second region of the filter, and/or through the membrane of the filter.

15. The dialysis supply system of claim 1, wherein the first, second, and third valves are controllable by the control unit to control a flow of disinfection fluid through the first, second, and third valves in a manner that allows the disinfection fluid to flow through the first and second regions of the filter.

16. The dialysis supply system of claim 1,
wherein the control unit is configured to control the first, second, and third valves in a manner such that, in the first mode, the first valve open, the second valve is closed, and the third valve is open.

17. The dialysis supply system of claim 1, further comprising a fourth valve arranged in a fourth fluid-conducting line coupled to the second region of the filter and to the first conduit, wherein, in the second mode, the control unit operates the fourth valve such that the fourth valve is open.

18. A dialysis system comprising:
at least one dialysis treatment unit;
a central dialysis liquid manufacturing unit that can be indirectly or directly coupled via a first conduit to the at least one dialysis treatment unit, the first conduit being configured to transport dialysis liquid from the central dialysis liquid manufacturing unit toward the dialysis treatment unit;
a filter having a first region and a second region, the first region of the filter being separated from the second region of the filter by a membrane;
at least three fluid-conducting lines branching off from the first conduit, wherein a first and a second fluid-conducting lines are coupled to the first region of the filter, and a third fluid-conducting lines is coupled to the second region of the filter such that the first and second fluid-conducting lines are bypassable by the third fluid-conducting line;
at least three valves disposed along the at least three fluid-conducting lines, respectively, the at least three valves being controllable by a control unit to control a flow of disinfection fluid through the valves in a manner that allows the disinfection fluid to flow through the first region of the filter, through the second region of the filter, and/or through the membrane of the filter; and
a single-use hydraulic module configured to be connected to the dialysis treatment unit and operable with the dialysis treatment unit to conduct, convey, process, mix, and/or equalize dialysis liquid,
wherein the control unit is configured to control the at least three valves in a manner such that, in a first mode, a first valve disposed along one of the first and the second fluid-conducting lines that is coupled to the first region of the filter is open, a second valve disposed along one of the first and the second fluid-conducting lines that is coupled to the first region of the filter is closed, and a third valve disposed along the third fluid-conducting line that is coupled to the second region of the filter is closed, and in a second mode, the first valve is closed, the second valve is open, and the third valve is open.

19. A dialysis supply system comprising:

at least one dialysis treatment unit;

a central dialysis liquid manufacturing unit that can be indirectly or directly coupled via at least a first conduit to the at least one dialysis treatment unit, the first conduit being configured to transport dialysis liquid from the central dialysis liquid manufacturing unit toward the dialysis treatment unit;

a filter having a first region and a second region, the first region of the filter being separated from the second region of the filter by a membrane;

at least three fluid-conducting lines branching off from the first conduit;

at least three valves disposed along the at least three fluid-conducting lines, respectively, the at least three valves being controllable by a control unit to control a flow of disinfection fluid through the valves in a manner that allows the disinfection fluid to flow through the first region of the filter, through the second region of the filter, and/or through the membrane of the filter;

a fourth valve controllable by the control unit to fluidly separate the dialysis treatment unit from the first conduit when the first conduit conducts disinfection fluid; and a single-use hydraulic module configured to be connected to the dialysis treatment unit and operable with the dialysis treatment unit to conduct, convey, process, mix, and/or equalize dialysis liquid.

20. The dialysis supply system of claim 19, wherein the fourth valve is positioned upstream of the at least one hydraulic module and positioned downstream of the filter, which is disposed within a fluid-conducting line coupled to the second region of the filter, and the filter is arranged between at least two of the valves.

21. The dialysis supply system of claim 20, wherein two of the four valves are arranged on a first side of the filter and two of the four valves are arranged on a second side of the filter.

* * * * *

UNITED STATES PATENT AND TRADEMARK OFFICE
CERTIFICATE OF CORRECTION

PATENT NO. : 9,259,522 B2  
APPLICATION NO. : 13/347011  
DATED : February 16, 2016  
INVENTOR(S) : Wolfgang Wehmeyer et al.

Page 1 of 1

It is certified that error appears in the above-identified patent and that said Letters Patent is hereby corrected as shown below:

In the Claims:

In column 11, line 37, Claim 2, delete "wherein-at" and insert --wherein at--.

In column 11, line 38, Claim 2, delete "of-the" and insert --of the--.

In column 11, line 51, Claim 5, delete "one-filter" and insert --one filter--.

In column 11, line 57, Claim 7, delete "0.1-0.5μm" and insert --0.1-0.5 μm--.

In column 12, line 21, Claim 16, after "first valve" insert --is--.

Signed and Sealed this  
Tenth Day of May, 2016

Michelle K. Lee  
*Director of the United States Patent and Trademark Office*